US005985280A

United States Patent [19]
Ritter et al.

[11] Patent Number: 5,985,280
[45] Date of Patent: Nov. 16, 1999

[54] DIAGNOSIS AND/OR THERAPY OF TUMOURS USING MONOCLONAL ANTIBODIES SPECIFIC FOR THE HUMAN IL-4 RECEPTOR

[75] Inventors: Mary Alice Ritter; Mark Larché, both of London, United Kingdom

[73] Assignee: Royal Postgraduate Medical School of Hammersmith Hospital, London, United Kingdom

[21] Appl. No.: 08/309,622

[22] Filed: Sep. 21, 1994

Related U.S. Application Data

[63] Continuation of application No. 07/922,007, Aug. 4, 1992, abandoned, which is a continuation of application No. 07/460,192, Feb. 6, 1990, abandoned, which is a continuation of application No. PCT/GB89/00359, Jan. 6, 1989.

[30] Foreign Application Priority Data

Apr. 6, 1988 [GB] United Kingdom .................... 8808015

[51] Int. Cl.$^6$ ...................... G01N 33/574; A61K 39/395; C07K 16/18

[52] U.S. Cl. ..................................... 424/154.1; 424/143.1; 424/144.1; 424/155.1; 435/7.23; 530/388.22

[58] Field of Search ................ 530/388.22; 435/240.27, 435/72.2, 70.21, 7.23; 424/143.1, 144.1, 155.1, 154.1, 183.1, 1.49

[56] References Cited

PUBLICATIONS

"Elevated Expression of the interleukin 4 receptor in carcinoma: a target for immunotherapy?", Br. J. Cancer (1989) 59, 910–914.
Osband et al., Immunology Today 11:193–195, 1990.
Harris et al. TIBTECH 11:42–44, 1993.
Dillman, Annals of Internal Medicine 111:592–603, 1989.
Hird et al., in Carney et al Eds "Genes and Cancer" John Wiley & Sons Ltd. 1990 pp. 183–189.
Waldman, Science 252:1657–1662, 1991.
De Maagd et al. Immunology 54: 745–754,1985.
Goding, J.W. *Monoclonal Antibodies* pp. 124–129 Academic Press 1983.

Primary Examiner—Toni R. Scheiner
Attorney, Agent, or Firm—Bacon & Thomas

[57] ABSTRACT

The invention provides compounds for use in the diagnosis and/or therapy of tumors and/or as an immunosuppressant agent selected from the group consisting of antibodies which bind to IL-4 receptors and IL-4 receptor-binding fragments thereof. A preferred such compound is monoclonal antibody MR6 produced by the hybridoma deposited at the European Collection of Animal Cell Cultures with the accession number 88033002. The invention also extends to the use of the compounds for in vitro removal of graft-versus-host reactive T-lymphocytes prior to bone marrow transplantation and to a novel protein of molecular weight 200,000 daltons functioning as a receptor for IL-4.

26 Claims, 3 Drawing Sheets

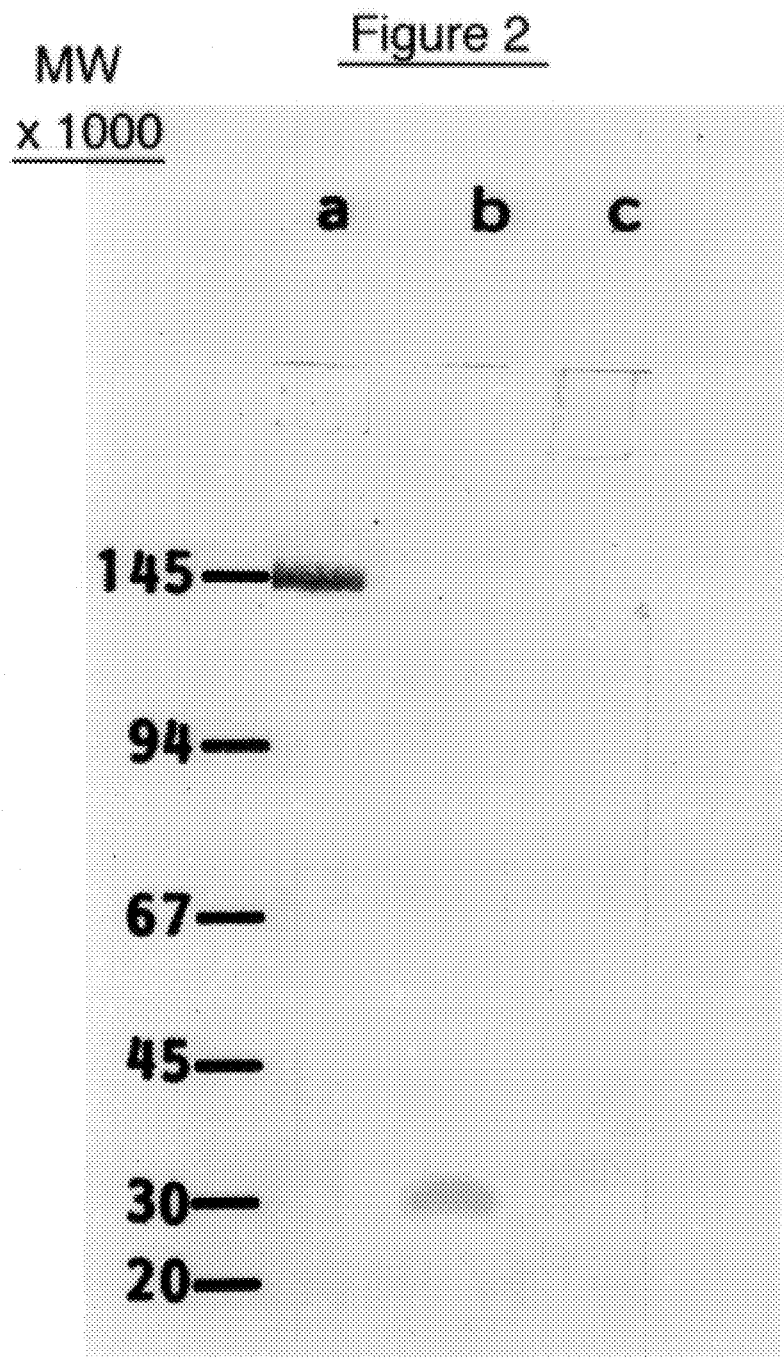
Figure 2: Western blotting analysis of thymocyte lysates using: (a) mAb MR6, (b) mAb CR3/43 directed against the beta-chain of the DRfamily, (c) irrelevant mAb second 4.7.

DIAGNOSIS AND/OR THERAPY OF TUMOURS USING MONOCLONAL ANTIBODIES SPECIFIC FOR THE HUMAN IL-4 RECEPTOR

This application is a Continuation of application Ser. No. 07/922,007, filed Aug. 4, 1992, now abandoned, which is a Continuation of application Ser. No. 07/460,192, filed Feb. 6, 1990, now abandoned which is a continuation of PCT/GB89/00359, filed Jan. 6, 1989.

The present invention relates to novel therapeutic and diagnostic agents.

Interleukin 4 (IL-4; previously known as B Cell Growth Factor (BCGF) or B Cell Stimulatory Factor 1 (BSF-1)) is a glycoprotein of molecular weight 15,000–20,000. It has pleiotropic effects, that is it induces T-lymphocytes to proliferate; it induces antigen-activated B lymphocytes to proliferate; it induces antigen-activated B lymphocytes to preferentially change the class of immunoglobulin that they secrete to IgE (the immunoglobulin class which mediates many allergic reactions); and it induces the up-regulation of expression of Class II Major Histo-compatibility Complex antigens on the surface of B lymphocytes (thereby enabling them to interact with helper T lymphocytes to augment the antibody response).

Receptors for IL-4 have been identified at very low levels on many cell types, for example T lymphocytes, B lymphocytes, monocyte/macrophage cells, epithelial cells and fibroblasts. It has not, however, previously been reported that IL-4 receptors were present at relatively high levels on neoplastic cells.

In the course of studies related to -the human thymus microenvironment, we have developed monoclonal antibodies which are found to bind to IL-4 receptors on cell surfaces and it has subsequently been found that such antibodies bind to sites on neoplastic cells which appear to be IL-4 receptor sites. This finding is of great significance in relation to the diagnosis and therapy of a wide range of malignant conditions, since the antibodies can be used as targeting vehicles for diagnostic or cytotoxic agents. Since neoplastic cells appear to express the IL-4 receptor at very much higher levels than normal cells, the action of such diagnostic or cytotoxic agents will thus be relatively specific and permit selective attachment of the agent to the neoplastic cells.

According to the present invention, therefore, we provide antibodies and fragments thereof binding to IL-4 receptors for use in the diagnosis and/or therapy of tumours and/or as immunosuppressive agents.

According to a further aspect of the invention, we provide such antibodies and fragments thereof having attached thereto at least one diagnostic and/or cytotoxic agent.

BRIEF DESCRIPTION OF THE DRAWINGS

FIG. 2, Row a is a Western Blotting analysis of thymocyte lysates using mAb MR6.

FIG. 2, Row b is a Western Blotting analysis of thymocyte lysates using mAb CR3/43 directed against the β-chain of the HLA-DR family.

FIG. 2, Row c is a Western Blotting analysis of thymocyte lysates using irrelevant mAb second 4.7.

Figure 1A:
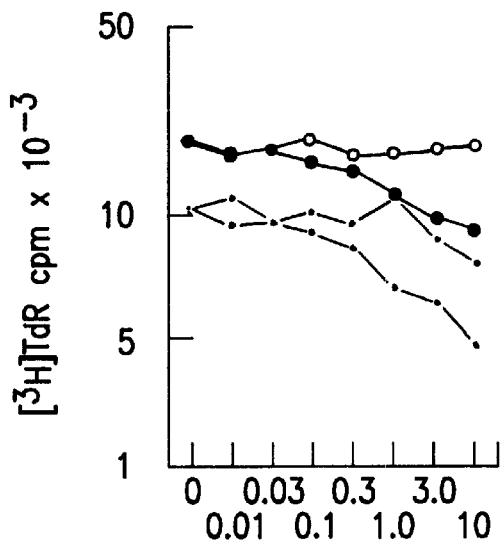
FIG. 1a demonstrates the inhibition of antigen and IL-2 induced proliferation of cloned human helper T-cells (clone HA1.7).

One group of anti IL-4 receptor (IL4R) antibodies has been developed using human thymic epithelial cells as antigens to generate hybridoma cell-lines and thence monoclonal antibodies. These antibodies were found to bind, in addition to human thymus epithelial cells, IL-4 receptor sites on other cells including T lymphocytes. Thus for example, the IL-4-induced T lymphocyte proliferation is completely blocked by the new monoclonal antibodies, indicating that they bind to substantially all IL-4 receptor sites on the cells. We have, in fact, observed additionally some blocking of the IL-2-induced response but believe that this is secondary to IL-4 receptor interaction. The monoclonal antibodies have been described by De Maagd et al (Immunology, 1985, 54 745). The anti IL-4R antibodies there described were given the code names MR3 and MR6. They were both IgG1 immunoglobulins which were found to bind to epithelial cells in the thymus cortex and keratin-negative cells in the medulla. F(ab')$_2$ fragments gave the same patterns of binding.

We have found that this antibody binds to a cell surface protein which, after conventional cell lysis and immunoprecipitation, has an approximate molecular weight of 145,000, which agrees, within the range of resolution of the techniques used, with the previously estimated molecular weight of the receptor to which radiolabelled IL-4 has been shown to bind. However, lysis of MR6-binding cells in the presence of a strong protease inhibitor such as PMSF (phenyl methyl sulphonyl fluoride) followed by immunoprecipitation shows that the protein to which MR6 binds has a molecular weight of about 200,000 daltons. Other work suggests that two shorter proteins (80,000 and 70,000 Daltons) may also be involved in IL-4 binding and the IL-4 receptor may in fact be a complex of three proteins. For simplicity, however, the expression 'IL-4 receptor' is used herein to refer to the 200,000 Dalton protein referred to above together with any further proteins involved in the IL-4 receptor function.

The full length 200,000 Dalton IL-4 receptor protein which we have isolated is new and constitutes a further feature of the invention. It is of use in the production of further monoclonal antibodies specifically binding to it, which anti IL-4 monoclonal antibodies may be used as described hereinafter in accordance with the invention.

In addition to the complete blocking of IL-4-induced proliferation of T lymphocytes, the antibody and fragments thereof also block IL-4-induced IgE production by antigen-stimulated B lymphocytes and thus act as an immunosuppressant.

We have found that, with the exception of thymic cortical epithelium, most epithelial cells bind little or none of the antibody. Surprisingly, however, our studies of neoplastic tissue have shown the antibody to react strongly with all types of carcinoma tissue tested (ovary, breast, colon, rectum, basal cell, squamous cell), with bronchoalveolar and small bowel adenocarcinoma and with haemopoietic malignancies such as cutaneous T cell lymphomas and other T and B cell lymphomas.

For use as a diagnostic agent, the anti IL-4R monoclonal antibody may be conjugated to an appropriate diagnostic agent. For scintigraphy, the antibody can be radiolabelled by known techniques with radioiodines, indium-111, gallium-67, technetium-99m or positron-emitting isotopes.

For use as a cytotoxic agent, the monoclonal antibody can be conjugated to a suitable cytotoxic material, for example a beta emitting radioisotope such as iodine-131, ytrium-90 etc., or alpha and auger emitting isotopes such as bismuth-212 and astatine. Other suitable cytotoxic substances include toxins such as abrin and ricin and toxic enzymes.

It will be appreciated that our novel finding that the IL-4R protein is expressed at high levels by neoplastic tissues makes it possible to use IL-4 itself as a targeting agent. Consequently, the invention additionally extends to IL-4 conjugated with one or more diagnostic and/or cytotoxic agents of the kinds disclosed above in relation to the monoclonal antibody, for use in the diagnosis and/or therapy of tumours.

We have further found that the monoclonal antibody, when added to a mixed lymphocyte culture of HLA mismatched donor and recipient cells (donor -v- irradiated recepient or recepient -v- irradiated donor), the subsequent generation of cytotoxic T lymphocytes with specificity for the target cells is blocked. In contrast, the generation of cytotoxic T cells directed against a third party target is unaltered. Since the expression of IL-4 receptors is normally low but is increased after antigen activation, it would appear that only those T lymphocytes with a high surface expression of IL-4 receptors are susceptible to the inactivation effects of the antibody. Thus, a major further use of the anti IL-4R antibody is as an antigen-specific, immunosupressive reagent for use in vitro for the removal of graft-versus-host reactive T lymphocytes prior to bone marrow transplantation and also in vivo in organ transplantation.

By virtue of its action against T-lymphocytes and B-lymphocytes stimulated to produce elevated levels of IL-4R, the monoclonal antibodies are also effective in inhibiting both B- and T-mediated allergic responses. Thus, for example, the production of IgE antibodies to house dust mite *D. farinae* is dependent on the presence of IL-4 and is blocked completely by MR6.

A still further use for the anti IL-4R antibody and fragments thereof is as an immunosupressive agent against autoimmune diseases. Such diseases are caused by the action of helper T-lymphocytes, B-lymphocytes and cytotoxic T lymphocytes being directed against host tissue which they do not recognise as self but react to as an antigen. These lymphocytes exhibit high levels of IL-4R expression when activated by antigens and are thus susceptible to blocking by the monoclonal anti IL-4R antibodies.

Anti IL-4R antibodies may be prepared by firstly immunising mice with human thymus epithelial cells (conveniently a homogenate of whole thymus) or cells exhibiting a high level of expression of IL-4R. The immunisation should be effected intraperitoneally; the first immunisation should be with Complete Freund's Adjuvant, while the second and subsequent immunisations should be with Freund's Incomplete Adjuvant. A minimum of three immunisations should be given at three to four week intervals. Three days after the last immunisation, spleen cells from the immunised mouse should be used with suitable non-producer myeloma cells such as NSO or P3×63-Ag8.653, using polyethylene glycol as a fusogen. Hybrid cells may be selected in an appropriate medium, e.g. HAT medium, and supernatant antibody activity may be tested in a primary screening system for ability to bind to thymic cortical epithelium in frozen sections of human thymus, using an immunohistochemical technique. Positive supernatants may then be subjected to a secondary immunofluorescence screen to detect those which can also bind to the surface of antigen-activated T lymphocytes (preferably a T cell clone). After cloning, by limiting dilution and re-screening, supernatants positive in the primary and secondary test may then be put into a tertiary functional test to assay for ability to block IL-4-induced proliferation of a T cell clone. The selected hybridoma can then be subjected to expansion to produce the antibody. The supernatant may, if desired, be subjected to purification, particularly when a diagnostic or cytotoxic agent is intended.

According to a further feature of the invention we provide cell-lines producing anti IL-4R monoclonal antibodies. These will commonly be hybridomas as described above. The hybridoma producing the mono-clonal antibody MR6 has been deposited at the European Collection of Animal Cell Cultures, Porton Down, Salsbury, Wiltshire, England on Mar. 30, 1988 with the accession number 88033002.

For attachment of radioisotopes to the antibody, it is possible to use any of the standard techniques. Thus, iodine may be introduced by the method of Solocinski, P. et al, (J. Endocrinol. 1979, 81, 131). Metals may be introduced by the method of Hnatowitch, D. T. et al, (J. Immunol. Meth. 1983, 65, 147). For conjugation with a cytotoxic substance, such as ricin or a toxic enzyme, known methods of conjugation using crosslinking agents may be used such as the method of Thorpe, P. E. and Ross, W. C. J. (Immunol. Rev. 1982, 62, 119).

The following Examples are given by way of illustration only:

EXAMPLE 1

Monoclonal Antibody MR6

Splenocytes from (CBA×BALBC)$F_1$ mice (Harlan Olac Ltd., Bicester, Oxon., UK) immunized with human thymic stromal homogenates were fused with the P3×63-Ag8.653 mouse plasmacytoma cell line (Flow Laboratories, Rickmansworth, Herts, UK) as described elsewhere (DeMaagd et al, Immunology, 1985, 54, 745). MR6 appears identical to MR3 antibody. Both are subclones of the same original parent clone and show substantially identical behaviour in all experimental systems tested.

Immunocytochemical Staining

Briefly, $5\mu$ cryostat sections of human paediatric thymus were fixed in acetone, incubated with 10 µg/ml mAb MR6 for 1–2 hr, and washed in phosphate-buffered saline (PBS). Bound antibody was detected using fluorescein isothiocyanate (FITC)-conjugated rabbit anti-mouse Ig, at 1/10 (Dakopatts, Denmark). Fluorescence was visualized using a Leitz UV microscope equipped with epi-illumination optics. Details of the technique have been described elsewhere (DeMaagd et al, 1985).

Western Blotting $10^8$ thymocytes or T cells, or 1 cm$^3$ of whole thymus were lysed in 300 µl and 1 ml respectively, of 10 mM Tris-HCl, 150 mM NaCl, pH 7.9, containing 0.5% NP40 and 10 µg/ml aprotonin. Lysates were incubated on ice for 15 minutes followed by centrifugation at 10,000 g for 6 minutes at room temperature, and were then subjected to SDS-PAGE in a 10% gel followed by electrophoretic transfer to a nitrocellulose membrane (Bio-Rad, Watford, Herts, UK). Unoccupied charged sites on the membrane were blocked by overnight incubation at 4° C. in PBS containing 2.5% skimmed milk powder (Marvel, Cadbury Schweppes, UK). PBS containing 0.5% skimmed milk powder was used subsequently for all antibody dilutions and for washing the membranes. Strips of the membrane were incubated for 2 hr with primary antibodies followed by washing for 15 minutes. Horseradish peroxidase-conjugated rabbit anti-mouse Ig antiserum (Dakopatts) was diluted 1/30 and incubated for 30 minutes with the membrane strips, followed by washing for 15 minutes. The peroxidase reaction was developed by first incubating the strips in 50 ml of 4-chloro-1-napthol (3 mg/ml in methanol, diluted 1:5 in Tris-buffered saline (TBS), pH 7.6) containing 2 mg/ml imidazole and 0.05% $H_2O_2$ until bands were visualized. Strips were then washed in TBS and further developed in TBS, pH 7.6, containing 0.6 mg/ml 3,3-diaminobenzidine and 0.05% $H_2O_2$. (All substrate reagents were from Sigma, Poole, Dorset).

T-Cell Clone HA1.7

The isolation and characterisation of clone HA1.7, which is reactive with the carboxyl terminus of the HA-1 molecule of influenza virus haemagglutinin (HA; residues 306–319), has been described in detail elsewhere (Lamb et al, Nature (Lond.) 300,66, 1982). Prior to use in proliferation assays, cloned T cells were rested for 7 days after the last addition of filler cells and antigen.

Inhibition Experiments

T cells of clone HA1.7 ($10^4$/well) were cultured with peptide 14 (p14; residues 306–319; 3 µg/ml) in the presence of inactivated autologous EBV-transformed B cells ($10^4$/well). Peripheral blood mononuclear cells ($5 \times 10^4$/well) were cultured with *Mycobacterium tuberculosis* soluble extract (MTSE; 3 µg/ml). Monoclonal antibodies MR6, anti-beta 2-microglobulin (negative control) (Becton-Dickinson, Mountain View, Calif.) or L243 anti-monomorphic HLA-DR (positive control) (ATCC, Rockville, Md.) were added at the initiation of these cultures at a concentration range of 0.01–10.0 µg/ml. Additionally, HA1.7 cells and PBMC were cultured alone with IL-2 (20% v/v) with or without the addition of mAb MR6 or anti-beta 2-microglobulin. The response of HA1.7 T cells to MR6 alone was also determined. After 60 hr (HA1.7), 72 hr (PBMC+IL-2) or 168 hr (PBMC+Ag), these having been the previously determined optimal culture periods, the cultures were pulsed with 1 micro Ci of tritiated methyl thymidine (($^3$H)TdR; Amershal International, Amersham, Bucks) for 8–16 hr and then harvested onto glass fibre filters. Proliferation, as correlated with ($^3$H)TdR incorporation, was measured by liquid scintillation spectroscopy. The results are expressed as the mean count per minute (cpm) for triplicate cultures with percentage error of the mean less than 20%. Background responses of T cells cultured with inactivated EBV-B cells or of EBV-B cells alone were less then 100 cpm.

Modulation Experiments

Following a 16 hr incubation of PBMC with MSTE antigen, with or without MR6 monoclonal antibody (10 µg/ml), samples were incubated with the following monoclonal antibodies: OKT3, OKT11 (Ortho Diagnostics) and anti-Tac (Amersham International), all used at approximately 10 µg/ml for 1 hr on ice, followed by washing in PBS and further incubation with a 1/10 dilution of FITC-conjugated rabbit anti-mouse Ig (Dakopatts). Cells were washed in PBS and analysed by Flow cytometry (EPICS-C; Coulter, Florida, USA).

RESULTS

MR6 mAb shows strong immunostaining of cortical epithelial cells and weaker staining of medullary, macrophages and dendritic cells (MØ/DC) in frozen: sections of thymus. Lymphocyte labelling is not apparent in tissue sections, but is seen clearly in suspension analysis (Larche et al, 1987). The whole antibody and the F(ab')$_2$ fragment of MR6 give identical staining patterns.

Western blotting analysis of thymocyte Nonidet P40 lysates with mAb MR6 defines a protein of relative molecular mass 145,000 (p145-MR6) (FIG. 2). Analysis of whole thymus (stromal cells and thymocytes) Nonidet P40 lysates gives the same 145,000 MW band on Western blots (data not shown). This was true for reduced as well as non-reduced sodium dodecyl sulphate-polyacrylamide gel electrophoresis, indicating the absence of a disulphide-linked polymeric structure.

In functional studies with the MHC class II-restricted T helper clone HA1.7, reactive with the carboxyl terminus (residues 306–319; p14) of influenza virus haemagglutinin (Lamb et al, 1982), addition of mAb MR6 at the same time as the proliferative signal was found to inhibit both antigen-induced and IL-2-induced proliferation in a dose-dependent fashion. In contrast, no inhibition was observed with a control antibody anti-beta 2-microglobulin, over the same concentration range. This was true for the response both to intact influenza virus (A/Texas) and to the immunogenic peptide. Since activation of the cloned T cells by IL-2 occurred in the absence of accessory cells, MR6 must act at the level of the T cell rather than the antigen-presenting cell. A similar dose-related pattern of inhibition by MR6 was seen with the response of PBMC to the soluble extract of Mycobacterium tuberculosis or with IL-2 alone (FIG. 1b). The inhibitory effect of MR6 on T-cell proliferation, therefore, is not unique to clone HA1.7 but also applies to uncloned cells. The negative control, anti-beta 2-microglobulin, antibody gave no inhibition of proliferation of PBMC to M. tuberculosis (data not shown). In contrast, the positive control cocktail of anti-HLA-DP, DQ and DR antibodies showed dose-dependent inhibition.

In modulation experiments the effect of pre-incubation with antigen and mAb MR6 on the T-cell phenotype (PBMC) was analysed by suspension immunofluorescence. Expression of the beta-chain of the IL-2 receptor (CD25, Tac) showed a small but consistent reduction (Table 1). No change in the expression of other cell surface molecules was observed. A similar MR6 antibody-induced reduction in Tac expression was observed for HA1.7-cloned T cells (data not shown).

TABLE 1

MR6 Antibody Induces Modulation of IL-2 Receptor Expression

| | Expression of IL-2 Receptor % Tac-positive cells | | % MR6-induced inhibition of |
|---|---|---|---|
| | Without MR6 | With MR6 | Tac Expression |
| Exp. 1 | 35 | 25 | 29 |
| Exp. 2 | 33 | 27 | 18 |
| Exp. 3 | 34 | 29 | 15 |
| Mean Value | 34* | 27* | 21* |

*The difference between these values is statistically significant, P is less than 0.05 (Student's t-test).

Peripheral blood mononuclear cells were incubated for 16 hrs with soluble extract of *M. tuberculosis*, with or without the addition of 10 µg/ml MR6 monoclonal antibody. Cells were then labelled in suspension by indirect immunofluorescence using anti-Tac monoclonal antibody followed by FITC-rabbit anti-mouse Ig, and analysed by flow cytometry (EPICS-C).

EXAMPLE 2

T Cell Proliferation Assays

T cells of clone Ha1.7 ($10^4$/well) were cultured with recombinant IL-4 (rIL-4, 250 U/ml; Glaxo, Greenford, Middlesex) in the presence of MR6 or negative isotype matched control antibody H17E2 (reactive with placental alkaline phosphatase) within the concentration range 0.0–10.0 μg/ml.

IL-4-dependent IgE Production

T cell clones reactive with Dermatophagoides farinae (house dust mite) were cultured with autologous E receptor negative (CD2 depleted) PBMC and allergen in the-presence of MR6 or negative control antibody H17E2.

Immunofluorescent Staining of T cell Clone HA1.7

Cells of clone HA1.7 were incubated with specific antigen as described earlier and stained with a panel of monoclonal antibodies at fixed time intervals therafter. Briefly, $10^6$ cells were incubated with 100 microliters of the following antibodies for one hour at 4° C., CD2, CD3, CD25, MR6 and H17E2 (negative control). Cells were washed for 10 minutes followed by incubation for 30 minutes at 4° C. with fluorescein isothiocyanate (FITC)-conjugated rabbit anti-mouse immunoglobulin [(FITC)-rabbit anti-mIg; Dakopatts, Copenhagen, Denmark] diluted 1/10. Finally, cells were washed for 10 mins and fixed in 1% paraformaldehyde (Sigma, Poole, Dorset) in phosphate-buffered saline (PBS). Staining was carried out at the following time intervals: zero, 4, 17, 24, 72 hrs and 7 days. Cells were analysed by flow cytofluorimetry (EPICS Profile, Coulter, Hialeah, Fla., USA).

RESULTS

Inhibition of IL-4-dependent T Cell Proliferation

Figure 3:
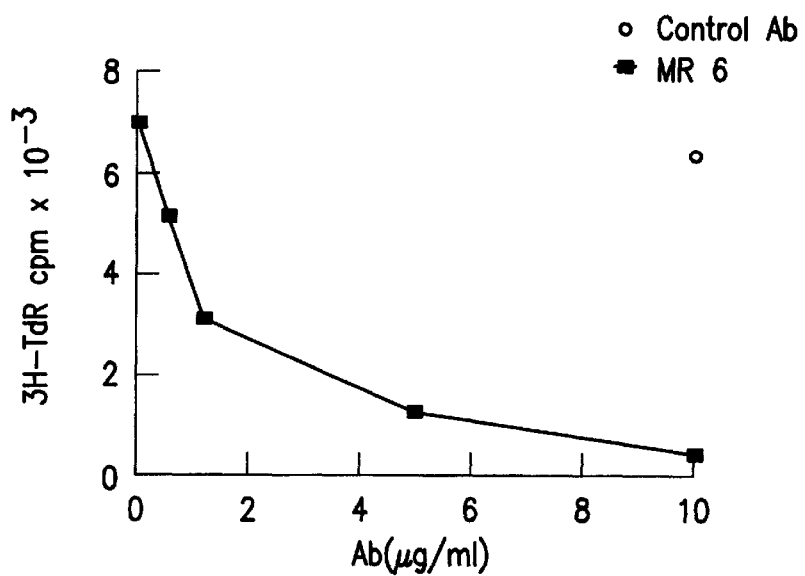
FIG. 3 shows the inhibitory effect of antibody MR6 on helper T-cells stimulated with IL-4.

Helper T cells of clone HA1.7 proliferated in a dose-dependent fashion when stimulated with IL-4. Addition of monoclonal antibody MR6 to cultures of clone Ha1.7 responding to optimal concentrations of IL-4, inhibited cellular proliferation in a dose-dependent fashion. A control antibody H17E2 directed against placental alkaline phosphatase had no effect on the proliferative response of these cells (FIG. 3).

Inhibition of IL-4-dependent IgE Production

Autologous E receptor negative cells produced IgE specific for antigenic determinants of Dermatophagoides farinae in the presence of either of two T cell clones. One T cell clone (DE9) required the addition of exogenous IL-4 in order to provide the necessary T cell "help" for IgE production, whilst the other clone (DE26) did not. However, IgE production by E receptor negative cells when incubated with the second clone could be enhanced by the addition of exogenous IL-4.

The addition of MR6 to these cultures at a final concentration of 2 μg/ml at the time of antigenic challenge and at day 5, gave 100% inhibition of IgE production. The negative control antibody H17E2 had no effect on IgE production (Table 2).

Kinetics of T Cell Surface Activation Molecules

Since it had been previously suggested that the IL-2R and IL-4R may co-modulate each others expression (Spits et al, 1987), it was of interest to determine the time course of lymphokine receptor expression and that of other T cell activation molecules following stimulation of T cells with antigen. Cells of clone HA1.7 were stained with either CD2, CD3, CD25 or MR6 at fixed time points after stimulation.

Figure 4:
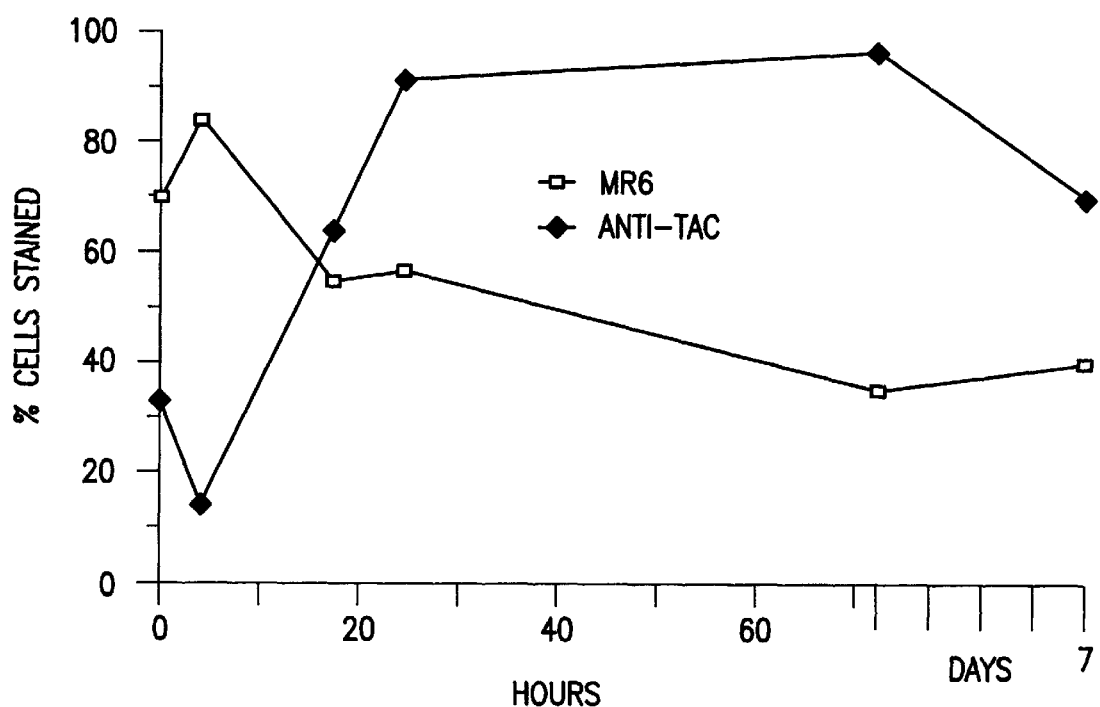
FIG. 4 shows the time course of lymphokine receptor expression by staining with antibody MR6 at fixed time points after stimulation with antigen.

Expression of the IL-2R was found to fall transiently 4 hrs after activation and then to rise to a peak at 24–48 hrs. In contrast MR6 staining rose immediately to peak at 4 hrs followed by a gradual fall (FIG. 4).

| Clone | E⁻ cells | Antigen | IL-4 | MR6 | IgE pg/ml | IgG ng/ml |
|---|---|---|---|---|---|---|
| DE26 | + | Df* | – | – | 309 | 347 |
| DE26 | + | Df | + | – | 439 | 546 |
| DE26 | + | Df | + | + | 0 | 211 |
| DE26 | + | Df | + | neg# | 283 | 296 |
| DE9 | + | Df | – | – | 0 | 145 |
| DE9 | + | Df | + | – | 150 | 330 |
| DE9 | + | Df | + | + | 0 | 0 |
| DE9 | + | G° | – | – | 0 | 0 |

*Df, Dermatophagoides farinae
°G, Mixed grass pollen (control allergen)
neg, negative control antibody, H17E2

EXAMPLE 3

Materials and Methods

The blocking effects of mAb MR6 were studied in four functional assays.

1. IL4 induced proliferation of cloned CD8 cytotoxic T cells. CD8 cloned T cells were incubated with their activating antigen and IL4 as a growth factor, in the presence or absence of mAb MR6.

2. Killing of targets by cytotoxic T cell clone. Since the cells used in this assay are antigen-activated mature cytotoxic T cells (Tc), the question to be answered by the addition of MR6 to these cultures is whether mAb MR6 has an inhibitory effect on the end point of the generation of Tc—the ability of the Tc to lyse its specific target.

3. The generation of Tc from pCTL in limiting dilution analyses (LDA), following primary stimulation with antigen. Here the data are measured in terms of the lysis of specific targets and are expressed as the frequency of specific pCTL present at the start of culture.

RESULTS

1. MR6 appeared to give complete inhibition of the IL4 induced proliferation of CD8 cloned T cells.

2. mAb MR6 had only a small inhibitory effect on the killing of targets by cytotoxic T cell clone 4C3.

3. mAB MR6 had a greater blocking effect on the generation of alloreactive Tc from pCTL, obtained from peripheral blood. This effect was considerably enhanced if MR6 was added 1 hour before the addition of antigen (genetically unrelated stimulator cells). For the responder/stimulator pair RHvRD the frequency of pCTL was reduced from 1:11,000 to 1:16,000 when MR6 was added at the same time as the antigen, and from 1:11,000 to 1:29,000 when MR6 was added 1 hour in advance of the antigen.

4. The inhibition of IL4 induced proliferation by MR6 shows that the antibody can act directly on cytotoxic T lymphocytes, rather than only acting indirectly via the helper T lymphocytes.

5. mAB MR6 has little effect on the actual killing process of targets by activated cloned Tc.

6. mAb MR6 has a partial inhibitory effect on the primary generation of Tc from their precursors, pCTL. This is enhanced if the cells are preincubated with MR6 for 1 hour prior to the addition of antigen.

EXAMPLE 4

Materials and Methods

1. Samples Tested with mAb MR6
   Normal Skin
   Lymphocyte Tumour of the Skin:
     Cutaneous T cell lymphoma (CTCL)
     T and B leukaemia and lymphoma cell lines
   Epithelial Tumours of Skin:
     Squamous cell carcinoma
     Squamous cell carcinoma in situ
     Basal cell carcinoma
     Bowen's disease
   Other Epithelial Tumours:
     Ovarian carcinoma
     Breast carcinoma
     Carcinoma of the rectum
     Carcinoma of the colon
     Bronchioalveolar adenocarcinoma
     Small bowel adenocarcinoma
     Thyroid adenocarcinoma
   Non-Epithelial Tumours:
     Mesothelioma
     Phaeochromocytoma
     Alveolar soft parts sarcoma
     Haemangiopericytoma
     Small intestine carcinoid 2. Immunofluorescence Staining Technique Frozen sections ($5\mu$) were cut and stained by indirect immunofluorescence for the presence of MR6, as described in DeMaagd et al, 1985. Some sections were also stained simultaneously for the presence of MR6 and keratin, using MR6 followed by an FITC-conjugated sheep anti-mouse Ig secondary reagent, and polyclonal rabbit anti-human keratin followed by a TMRITC-conjugated swine anti-rabbit secondary reagent. The method for this dual immunofluorescence staining is also described in DeMaagd et al, 1985. Some sections of normal skin were also labelled for the simultaneous presence of MR6 and NaI/34 (a marker of epidermal Langerhans cells). Since MR6 ia mouse IgG1 mAb and NaI/34 is a mouse IgG2a mAb, secondary reagents were used that could specifically distinguish between these two immunoglobulin subclasses. Hence MR6 was detected using FITC-conjugated sheep anti-mouse IgG1 and NaI/34 was detected using TMRIC-conjugated rabbit anti-mouse IgG2a.

3. Western Blotting Analysis

One sample of ovarian carcinoma was homogenised and solubilised in NP40. The lysate was separated by SDS-PAGE and blotted on to a nitrocellulose membrane. The paper was cut into strips which were incubated in either MR6 or a negative control mAb (IgG1 subclass, but does not bind to the tumour cells), followed by a peroxidase-conjugated secondary reagent and development in DAB.

RESULTS

1. Normal Skin

No epidermal (=epithelial) cells in samples of normal skin were MR6+. The only MR6+ cells in normal skin were dendritic-like cells. Dual immuno-fluorescence using MR6 and NaI/34 showed that all these MR6+ cells wer also NaI/34; however, only approximately 50% of NaI/34+ cells were also MR6+. Hence MR6 is on a subpopulation of epidermal Langerhans cells.

2. Immunofluorescence Analysis of Epithelial Tumours of the Skin

Four epithelial tumours of the skin were analysed and each was found to be strongly MR6 positive. Within each tumour, essentially all cells were MR6+. Dual immunofluorescence analysis with MR6 and the polyclonal rabbit anti-keratin antibody showed that all MR6+ cells were also keratin+, and that essentially all keratin+ cells were also MR6+. This confirms that the molecule detected by MR6 is present on the epithelial tumour cells (Data are summarized in Table 3).

3. Immunofluorescence of Cutaneous T Cell Lymphoma (CTCL)

One sample of CTCL was analysed for MR6 expression. Essentially all the neoplastic lymphocytes were strongly MR6+. In addition, the basal epithelial cell layer of the epidermis was weakly MR6+.

4. Immunofluorescence Analysis of Other Epithelial and Non-Epithelial Tumours

Several samples of carcinomas from organs other than the skin were studied. Samples of non-epithelial tumours were also analysed. All carcinomas tested were found to be MR6+; in these cases the majority of the neoplastic epithelial cells were MR6+. None of the non-epithelial tumours were MR6+. (Data are summarized in Table 3).

5. Western Blotting Analysis of Ovarian Carcinoma

Western blotting analysis of the ovarian carcinoma sample with MR6 showed a single band of approximate molecular weight 145,000. This was indistinguishable from the 145K band seen for MR6 on thymocytes and whole thymus (thymocytes, epithelial cells and dendritic cells).

These data show the following:

1. The only detectable MR6+ cell in frozen sections of normal healthy human skin is the epidermal Langerhans cell. This finding is consistent with our previous observations that mAb MR6 binds to macrophages/dendritic cells in the medulla of the thymus and suggests that it is thymic dendritic cells rather than macrophages that are MR6+. Dendritic cells, by processing and presenting antigen to T lymphocytes, play a vital part in T lymphocyte activation.

2. Analysis of epithelial tumours of the skin showed that all samples tested were strongtly MR6+; this contrasts with the situation in normal skin where no epithelial cells are MR6+. In addition, the lymphocytes in CTCL were strongly labelled with mAb MR6; again this contrasts with normal skin, where in tissue sections the level of expression of the MR6 antigen is below the detection level of immunohistochemical techniques (although when analysed in cell suspension, peripheral T lymphocytes have been shown to be MR6+). When a larger series of carcinomas and non-epithelial tumours were studied, only those tumours that were of epithelial origin were positive with mAb MR6. However, no lymphoid or haemopoietic neoplasms were included in this series. We have also studied the binding of mAb MR6 to a wide range of normal epithelia. Our data so far indicate that the majority of the latter are either negative (e.g. skin, tonsil, lung, gut) or very weakly positive (e.g. convoluted tubules in the kidney) for MR6. Cortical epithelium in the thymus (the immunogen against which mAb MR6 was raised) appears to be the exception in being strongly MR6+.

3. Western blotting analysis shows that the molecule to which MR6 binds on epithelial carcinoma cells is indistinguishable from that to which it binds in thymus.

4. Thus if MR6 is detecting the IL4 or related growth factor receptor, the elevated expression of p145-MR6 on CTCL and carcinomas might be responsible for the excessive proliferation of these tumour cells; p145-MR6 would therefore be acting as an oncogene product.

5. The elevated expression of p145-MR6 in neoplasia indicates that mAb MR6 may be of considerable clinical potential in the diagnosis and therapy of these diseases.

TABLE 3

| MR6+ Tumours | MR6− Tumours |
| --- | --- |
| Ovarian carcinoma (x4) | Mesothelioma (x2) |
| Carcinoma of breast | Phaeochromocytoma (x2) |
| Carcinoma of rectum | Alveolar soft parts sarcoma |
| Carcinoma of colon | Haemangiopericytoma |
| Basal cell carcinoma | Small intestine carcinoid |
| Bowen's carcinoma | |
| Squamous cell carcinoma in situ | |
| Squamous cell carcinoma | |
| Bronchoalveolar adenocarcinoma | |
| Small bowel adenocarcinoma | |
| Cutaneous T cell lymphoma | |

Frozen tissue sections were analysed for binding of mAb MR6, using an indirect immunofluorescence technique. Sections were scored for whether the tumour cells were MR6+ or MR6−. Where a tumour showed MR6 binding, the majority of the cells were found to be MR6+.

Key x4—samples from 4 different patients were analysed.

x2—samples from 2 different patients were analysed.

EXAMPLE 5

Induction of Tolerance in a CTL-P Assay Using MR6

Method

A normal, HLA mismatched pair is chosen and peripheral blood taken. PBMCs are separated as usual, and an LDA assay performed between the responder and stimulator and third party.

A bulk culture is then set up between the responder and stimulator, using $20–25 \times 10^6$ responder cells, an equal number of stimulator cells which have been irradiated (so that they can stimulate but not respond in this assay) and approximately 1 ml of MR6 supernatant per $10^6$ responder cells, all at a total cell concentration of $1 \times 10^6$ cells/ml. This is incubated for 48 hours, washed and incubated in AB medium for 1.5 hours to remove all MR6. It is then washed again and counted.

The residual responder cells are then set up in another LDA assay against the original stimulator and a third party control.

The LDA was a 7 day assay in each case, with $5\mu$/ml of rIL2 being added on day 3.

RESULTS

Experiment 1

| Responder (Donald P) A2 B44 DR2 | -v- | Stimulator (Edward K) A9,29 B12,21 DR5,7 |
| --- | --- | --- |
| CTL-P before bulk culture: | | 1:18,300) 94% reduction in frequency |
| CTL-P after bulk culture: with MR6 | | 1:329,000) |

Experiment 2

| Responder (Mark L) A2,3 B7,44 DR2,4 | -v- | Stimulator (Edward K) A9,29 B12,21 DR5,7 |
| --- | --- | --- |
| CTL-P before bulk culture: | | 1:9,800) 98% reduction in frequency. |
| CTL-P after bulk culture: with MR6 | | (1:590,000) |
| Responder (Mark L) A2,3 B7,44 DR2,4 | -v- | Third Party Control (Mary R) A1,26 B44,27 DR5 |
| CTL-P before bulk culture: | | 1:9,800) |
| CTL-P after bulk culture: with MR6 | | 1:10,000) | mAb MR6 has a dramatic effect on the generation of Tc when the secondary response is assayed by LDA. In this system, the frequency of antigen-specific pCTL was reduced by 98%, to a level that would be considered non-responsive. This inhibition was specific for the antigen used to activate the primary bulk cultures, no inhibition was seen against a third party target. Thus, used in this way, MR6 can induce antigen-specific immunological unresponsiveness. We have preliminary data indicating that MR6 exerts its effect by inactivating rather than killing the cells to which it binds, since the addition of MR6 does not increase the number of dead cells in the cultures.

The clinical implications of these findings are considerable. The ultimate goal of all transplant immunologists is to induce antigen-specific immunological tolerance, and although drugs such as Cyclosporin A have gone some way towards solving the problem of graft rejection, this immunosuppression is not antigen specific and carries with it various side effects such as its nephrotoxity. Thus, mAb MR6 could be of potential use as an antigen-specific immunosuppressive reagent for use in vivo in organ transplantation to prevent graft rejection, and in vitro for specifically depleting donor bone marrow of anti-host reactive cells prior to bone marrow transplantation in order to prevent the development of lethal graft-versus-host disease.

EXAMPLE 6

IMMUNOPRECIPITATION

Cell Surface Iodination

Materials 50 ml polypropylene centrifuge tubes (Falcon 2070).

1 ml Eppendorf microfuge tubes.

Lactoperoxidase (Sigma L-2005; 10 mg/ml in PBS).

Hydrogen peroxide 30% solution (Sigma H-1009; 1/1000 in PBS).

$^{125}$Iodine (Amersham International IMS.30; 1.5 mCi per $10^8$ cells).

Buffers

A. Phosphate-buffered saline (PBS).

B. Lysis buffer [10 mM Tris pH 7.4, 1 mM $MgCl_2$, 10 $\mu$g/ml Aprotonin (Sigma A-6279), 1 mM phenyl methyl sulphonyl fluoride (PMSF; Sigma P-7262), 0.5% Nonidet P-40 (NP-40; Sigma N-6507)].

C. Dialysis buffer (0.15 M NaCl, 10 mM Tris pH 7.4).

D. Sepharose washing buffer (PBS containing 0.5% NP-40).

E. Immunprecipitate washing solution (0.5% NP-40, 0.1% sodium dodecyl sulphate (SDS; Sigma L-4509), 0.5 M NaCl, 10 mM ethylene diamine tetra-acetic acid (EDTA), 50 mM Tris pH 8.0).

F. Sample buffer for electrophoresis (0.5 ml 10% SDS, 0.5 ml glycerol, 0.4 ml 1 M Tris pH 6.8, 500 µl 0.1% bromophenol blue, 3.1 ml $H_2O$).

Cells expressing relevant surface antigens were grown in tissue culture or obtained from fresh tissue.

Approximately $10^8$ cells were labelled for each subsequent precipitation.

Cells were washed twice in ice-cold PBS and resuspended in 1 ml of PBS in a 50 ml tube. 50 µl of lactoperoxidase solution was added to the cell suspension followed by 15 µl of $^{125}I$ (100 mCi/ml) and 50 µl of $H_2O_2$. The cell suspension was left at room temperature for 15 minutes and the addition of $H_2O_2$ repeated. After a further 15 minute incubation at room temperature, the tube was filled with ice-cold PBS and centrifuged for 10 minutes at 500 g. The cell pellet was resuspended very gently in ice-cold lysis buffer. The whole lysate was then transferred to an eppendorf microfuge and incubated on ice for 15 minutes prior to high speed centrifugation for 5 minutes at 4° C. The lysate was then dialysed twice over an 18 hour period against dialysis buffer (as above).

Precipitation

Following dialysis the lysate was microfuged for 5 minutes at 4° C. The supernatant was then pre-cleared using a mixture of protein A beads and non-specific serum. Initially non-immune mouse serum was added to the lysate (2–5% by volume) and mixed for 3 hours (or overnight) at 4° C. 30–50 µl of packed protein A beads were then added and incubated for a further 3 hours. The lysate was then microfuged and a further aliquot of protein A beads added to the supernatant. After 3 hours the protein A beads were microfuged out of the lysate and specific antibody (2–5% ascites or 100–200 µg of purified antibody) was added for 3 hours or overnight at 4° C. followed by precipitation of the antibody-antigen complexes by addition of a 30–50 µl aliquot of protein A beads, incubation for 3 hours and finally microfugation. The pelleted beads were then washed 3–5 times in immunoprecipitate washing buffer to remove all non-specific labelled molecules. Beads were then mixed with 40–50 µl of sample buffer, boiled for 3 minutes and microfuged. Samples were loaded onto a 7% polyacrylamide gel and electrophoresed overnight at a constant voltage of 50 volts.

Following electrophoresis, gels were stained with Coomassie brilliant blue R (Raymond A. Lamb; BDH) for a minimum of 2 hours. Gels were then destained using a 50% methanol, 10% acetic acid and 40% water solution followed by drying under vacuum. The dried gel was then placed next to an X-ray film (Kodak Ortho G, 18–24 cm) in a light tight autoradiography cassette and stored at –70° C. for 4–7 days prior to development.

Following the above procedure and using monoclonal antibody MR6 as specific antibody, autoradiography showed the presence of a molecule of molecular weight approximately 200,000 Daltons which binds to MR6. This contrasts with results obtained in the absence of protease inhibitors such as PMSF, where the molecule binding to MR6 had a molecular weight of about 145,000 Daltons, consistant with prior art reports.

EXAMPLE 7

Tumour Imaging

Monoclonal antibody MR6 produced as a bulk supernatant by tissue culture of the hybridoma deposited at the European Collection of Animal Cell Cultures under the accession number 88033002 and purification by protein A affinity chromatography was coupled to Indium[111] using the cyclic anhydride of diethylene-triamine pentaacetic acid (DTPA, Sigma UK) by the method of Huatowich et al (Science 220, 613). One adult male patient with carcinoma of the lung was given an intravenous dose of 0.5 mg MR6 labelled with 1.2 mCi $^{111}$In and a gamma-camera scan performed immediately and after 24 and 48 hours. Anterior, posterior and whole body scans were taken each time. It was shown that immediately after administration, MR6 activity was available throughout the blood pool but that this cleared to reveal significant uptake of MR6 into the tumour site after 48 hours.

Figure 1B:
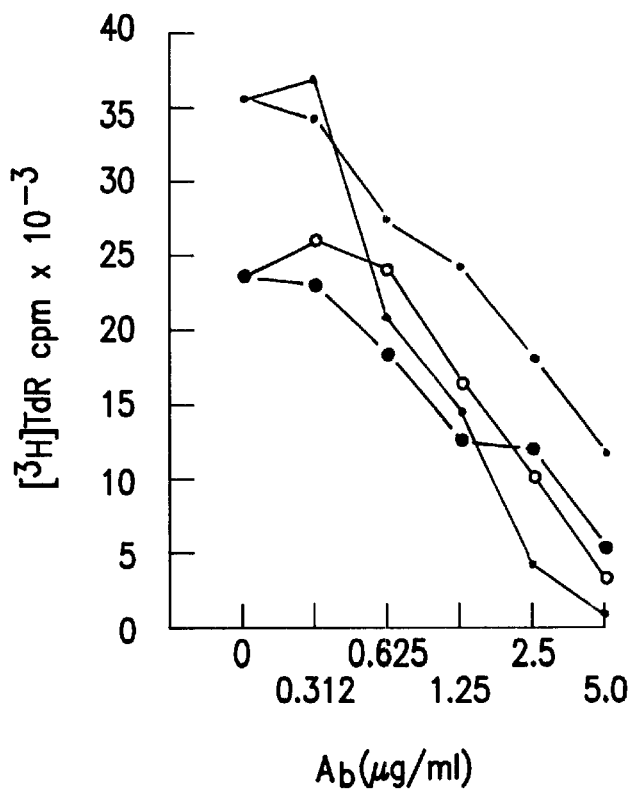
FIG. 1b demonstrates the inhibition of antigen and IL-2 induced proliferation of peripheral blood mononuclear cells.

Legends to FIGS. 1 and 2

FIG. 1

Inhibition of antigen and IL-2 induced proliferation of: (a) Cloned human helper T cells (clone HA1.7). Antigen (peptide 14)-induced proliferation is inhibited by mAb MR6 (o----o) but not by monoclonal anti-proliferation is also inhibited by mAb MR6 (----) Addition of anti-beta 2-microglobulin shows no inhibition of the proliferative response to IL-2 (----). The addition of MR6 to HA1.7-cloned T cells in the absence of either antigen or IL-2 does not induce proliferation (----). (b) Peripheral blood mononuclear cells. Antigen-induced proliferation is inhibited by mAb MR6 (----) and mAb L243 (anti-monomorphic HLA-DR; ----). IL-2-induced proliferation also inhibited by mAb MR6 (----) and mAb L243 (----).

FIG. 2

Western blotting analysis of thymocyte lysates using: (a) mAb MR6, (b) mAb CR3/43 directed against the beta-chain of the HLA-DR family, (c) irrelevant mAb second 4.7.

We claim:

1. A method for the diagnosis of tumours characterised by elevated expression of an about 200,000 dalton protein which binds to antibody produced by the hybridoma deposited at the European Collection of Animal Cell Cultures with accession number 88033002; wherein said method comprises administering to a human subject an effective amount of an agent selected from the group consisting of an antibody which specifically binds to the about 200,000 dalton protein, a fragment of said antibody which is capable of specifically binding to said 200,000 dalton protein, and mixtures thereof, whereby said agent becomes bound to said about 200,000 dalton protein of said tumours; and then detecting the presence of said agent bound on or in said tumours.

2. A method as claimed in claim 1 wherein said agent is attached to at least one diagnostic agent.

3. A method as claimed in claim 2 in which the diagnostic agent is a radioiodine, indium-111, gallium-67, technetium-99m or a positron emitting radioisotope.

4. A method as claimed in claim 1 in which the antibody is a monoclonal antibody binding to the epithelial cells in the thymus cortex and keratin-negative cells in the medulla.

5. A method as claimed in claim 1 in which said antibody is monoclonal antibody MR6 produced by the hybridoma deposited at the European Collection of Animal Cell Cultures with accession number 88033002 wherein said monoclonal antibody is a monoclonal antibody binding to the epithelial cells in the thymus cortex and keratin-negative cells in the medulla.

6. A method as claimed in claim 1 in which said tumors are epithelial tumors or haemopoietic malignancies.

7. A method of therapy of tumors characterized by elevated expression of an about 200,000 dalton protein which binds to antibody produced by the hybridoma deposited at the European Collection of Animal Cell Cultures with accession number 88033002. wherein said method comprises administering to a human subject a therapeutically effective amount of an agent selected from the group consisting of an antibody which specifically binds to the about 200,000 dalton protein, a fragment of said antibody which is capable of specifically binding to said 200,000 dalton protein, and mixtures thereof.

8. A method as claimed in claim 7 wherein said agent is attached to at least one cytotoxic agent.

9. A method as claimed in claim 8 in which the cytotoxic agent is a beta-emitting radioisotope, an alpha or auger emitting radioisotope or a toxin.

10. A method as claimed in claim 7 in which the antibody is a monoclonal antibody binding to the epithelial cells in the thymus cortex and keratin-negative cells in the medulla.

11. A method as claimed in claim 10 in which said antibody is monoclonal antibody MR6 produced by the hybridoma deposited at the European Collection of Animal Cell Cultures with accession number 88033002.

12. A method as claimed in claim 7 in which said tumors are epithelial tumors or haemopoietic malignancies.

13. A method of therapy of an activated immune response characterized by elevated levels of expression of an about 200,000 dalton protein on cells involved in the immune response wherein a human subject is administered an effective amount of an agent selected from the group consisting of an antibody which specifically binds to the about 200,000 dalton protein, a fragment of said antibody which is capable of specifically binding to said 200,000 dalton protein, and mixtures thereof; with the proviso that said 200,000 dalton protein binds to antibody produced by the hybridoma deposited at the European Collection of Animal Cell Cultures with accession number 88033002.

14. A method as claimed in claim 13 wherein said agent is attached to at least one cytotoxic agent.

15. A method as claimed in claim 14 in which the cytotoxic agent is a beta-emitting radioisotope, an alpha or auger emitting radioisotope or a toxin.

16. A method as claimed in claim 13 in which the antibody is a monoclonal antibody binding to the epithelial cells in the thymus cortex and keratin-negative cells in the medulla.

17. A method as claimed in claim 16 in which said antibody is monoclonal antibody MR6 produced by the hybridoma deposited at the European Collection of Animal Cell Cultures with accession number 88033002.

18. A method for achieving antigen-specific immunosuppression in a human subject in vivo or in human cells or tissues in vitro wherein said human subject, cells or tissues are administered antigen for presentation and are subsequently administrated an effective amount of an agent selected from the group consisting of an antibody which specifically binds to an about 200,000 dalton protein, a fragment of said antibody which is capable of specifically binding to said 200,000 dalton protein, and mixtures thereof, wherein the cells to be immunosuppressed are specific for the presented antigen and are characterized by elevated levels of expression of said 200,000 dalton protein; with the proviso that said 200,000 dalton protein binds to antibody produced by the hybridoma deposited at the European Collection of Animal Cell Cultures with accession number 88033002.

19. A method as claimed in claim 18 wherein said agent is attached to at least one cytotoxic agent.

20. A method as claimed in claim 19 in which the cytotoxic agent is a beta-emitting radioisotope, an alpha or auger emitting radioisotope or a toxin.

21. A method as claimed in claim 18 in which the antibody is a monoclonal antibody binding to the epithelial cells in the thymus cortex and keratin-negative cells in the medulla.

22. A method as claimed in claim 21 in which said antibody is monoclonal antibody MR6 produced by the hybridoma deposited at the European Collection of Animal Cell Cultures with accession number 88033002.

23. The method of claim 13 wherein said activated immune response is an autoimmune response wherein said cells involved in the activated immune response are cells which do not recognize host tissue as self and which are thereby reactable with host tissue as antigen; said cells reactable with host tissue as antigen being selected from the group consisting of helper T-lymphocytes, B-lymphocytes and cytotoxic T-lymphocytes; whereby said antibody which binds with said about 200,000 dalton protein on said cells inhibit said autoimmune response.

24. The method of claim 13 wherein said activated immune response is a B- or T-mediated allergic response wherein said cells involved in said allergic response are selected from the group consisting of B-lymphocytes and T-lymphocytes which produce IgE antibodies to an allergin wherein said antibody which binds with said about 200,000 dalton protein on said cells inhibit the production of said IgE antibodies.

25. The method of claim 18 wherein said agent is administered in vivo to a person undergoing organ transplant wherein said agent is an antigen specific immunosuppressive reagent which inactivates graft-versus-host T-lymphocytes.

26. The method of claim 18 which is conducted on bone marrow tissue in vitro prior to transplantation of said tissue into a recipient whereby said agent is an antigen specific immunosuppressive reagent which inactivates graft-versus-host reactive T-lymphocytes.

* * * * *